United States Patent
Bombardelli et al.

(10) Patent No.: US 7,078,432 B2
(45) Date of Patent: *Jul. 18, 2006

(54) PROCESS FOR THE PREPARATION OF THE 14β-HYDROXY-BACCATIN III-1,14-CARBONATE

(75) Inventors: Ezio Bombardelli, Milan (IT); Gabriele Fontana, Milan (IT); Maria Luisa Gelmi, Milan (IT); Donato Pocar, Milan (IT)

(73) Assignee: Indena S.p.A., Milan (IT)

( * ) Notice: Subject to any disclaimer, the term of this patent is extended or adjusted under 35 U.S.C. 154(b) by 47 days.

This patent is subject to a terminal disclaimer.

(21) Appl. No.: 10/492,986

(22) PCT Filed: Jul. 18, 2002

(86) PCT No.: PCT/EP02/08005

§ 371 (c)(1),
(2), (4) Date: Aug. 18, 2004

(87) PCT Pub. No.: WO03/035633

PCT Pub. Date: May 1, 2003

(65) Prior Publication Data

US 2004/0266859 A1 Dec. 30, 2004

(30) Foreign Application Priority Data

Oct. 19, 2001 (IT) .................... MI2001A002186

(51) Int. Cl.
*A61K 31/337* (2006.01)
*C07D 35/14* (2006.01)
*C07D 305/00* (2006.01)
*C07D 307/77* (2006.01)
*C07D 317/08* (2006.01)

(52) U.S. Cl. ............... 514/449; 549/510; 549/511; 549/229; 549/230; 549/297; 514/449

(58) Field of Classification Search ............... 549/229, 549/230, 297, 510, 511; 514/449
See application file for complete search history.

(56) References Cited

U.S. PATENT DOCUMENTS

| 5,705,508 A | 1/1998 | Ojima et al. ............ 514/320 |
| 6,737,534 B1 * | 5/2004 | Pontiroli et al. ............ 549/296 |
| 2005/0020669 A1 * | 1/2005 | Bombardelli et al. ....... 514/449 |

FOREIGN PATENT DOCUMENTS

| EP | 559 019 | 9/1993 |
| WO | WO 96 29321 | 9/1996 |
| WO | WO 96 30373 | 10/1996 |
| WO | WO 96 36622 | 11/1996 |
| WO | WO 97 43291 | 11/1997 |
| WO | WO 98 30553 | 7/1998 |
| WO | WO 02/44161 | * 11/2001 |
| WO | WO 02 12215 | 2/2002 |

* cited by examiner

*Primary Examiner*—D. Margaret Seaman
*Assistant Examiner*—Niloofar Rahmani
(74) *Attorney, Agent, or Firm*—Young & Thompson

(57) ABSTRACT

A process for the preparation of 14β-hydroxy-baccatin III-1,14-carbonate useful for the preparation of novel taxane derivatives with antitumor activity.

20 Claims, No Drawings

PROCESS FOR THE PREPARATION OF THE 14β-HYDROXY-BACCATIN III-1,14-CARBONATE

The present invention relates to a process for the preparation of 14β-hydroxy-1,14-carbonate-baccatin III. The product obtained with the process of the invention can be used in the preparation of novel taxane derivatives with antitumor activity.

Taxanes are one of the most important classes of antitumor agents developed in recent years. Paclitaxel is a diterpene complex obtained from the bark of *Taxus brevifolia* and is considered one of the major medicaments for the therapy of cancer. At present, an extensive search is being carried out for novel taxane derivatives having superior pharmacological activity and improved pharmacokinetic profile. A specific approach relates to baccatin III derivatives variously modified with respect to the parent structure. Examples of said compounds are represented by the 14β-hydroxy baccatin III derivatives disclosed in U.S. Pat. No. 5,705,508, WO 97/43291, WO 96/36622. At present, 14β-hydroxy-deacetyl-baccatin III 1,14-carbonate derivatives are prepared starting from the precursor 14β-hydroxy-deacetylbaccatin III, which is a natural compound obtainable in small amounts by extraction of the leaves of *Taxus wallichiania*, as disclosed in EP 559 019. There is strong need for novel processes for the easy, effective preparation of large amounts of 14β-hydroxy-1,14-carbonate-baccatin III, and hence the derivatives thereof.

It has now been found that 14β-hydroxy-baccatin III-1,14-carbonate can be prepared with a process starting from 13-ketobaccatin III, which compound can be easily obtained from 10-deacetylbaccatin III, which can in turn be easily isolated in large amounts from the leaves of *Taxus baccata*, contrary to 14β-hydroxy-baccatin III.

Therefore, the invention relates to a process for the preparation of 14β-hydroxy-baccatin III-1,14-carbonate which comprises the following steps:

a. treatment of 7-triethylsilyl-13-ketobaccatin III of formula

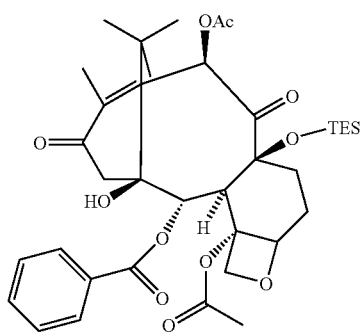

with suitable bases and oxidizing agents, to give 7-triethylsilyl-13-keto-14-hydroxy-baccatin III:

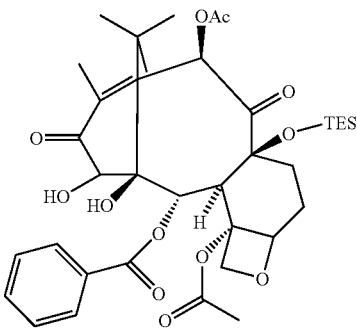

b. carbonation of the 1 and 14 hydroxyls to give 14β-Hydroxy-7-triethylsilyl-13-keto-baccatin III-1,14-carbonate:

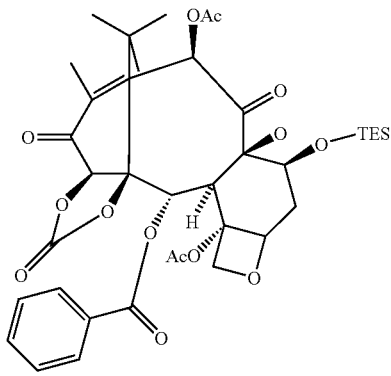

c. reduction of the ketone at the 13-position and cleavage of the protecting group in 7.

Starting 13-ketobaccatin III is conveniently protected at the 7-position with a suitable protective group, preferably selected from silyl ethers (preferably triethylsilyl ether). Step a) is carried out by treatment with a suitable base, in particular potassium t-butoxide (t-BuOK) or potassium bis(trimethylsilyl)amide (KHMDS). The reaction can be carried out at −40 to −78° C. Suitable solvents for this reaction are ethers, such as tetrahydrofuran or diethyl ether, in particular in mixture with hexamethylphosphoramide (HMPA) or 1,3-dimethyl-3,4,5,6-tetrahydro-2(1H)pyrimidinone (DMPU). The enolate is then treated with an oxidizing agent, such as oxaziridine derivatives (in particular N-benzenesulfonyl phenyl oxaziridine, N-benzenesulfonyl m-nitrophenyl oxaziridine and camphorsulfonyloxaziridine) to provide the 7-protected 13-keto-14-hydroxy-baccatin III derivative.

Step b) is then carried out by treatment with a carbonylating agent (for example carbonyldiimidazole or phosgene) under the conditions usually described in literature, to provide the 1,14-carbonate derivative. The reaction can be conveniently carried out in inert solvents, preferably ethers or chlorinated solvents, in the presence of a base (preferably pyridine or triethylamine), at a temperature ranging from −40° C. to room temperature. The reaction can be carried out both on the pure starting material and on the crude from the previous step.

The reduction of the carbonyl at the 13-position of step c) is easily carried out with sodium borohydride in ethanol at a temperature usually ranging from −20 to −50° C., and is completed within 2–6 hours. The reaction can also be carried out in methanol, isopropanol, or in a methanol and tetrahydrofuran mixture. The reducing agent can be used in stoichiometric amount, although an excess of hydride is preferably used. The reduction can also be effected with other hydrides, preferably tetrabutylammonium borohydride, lithium borohydride, sodium triacetoxy borohydride, in the conditions known in the art.

Protection at the 7-position is removed under conditions depending on the protective group used. For example, if the protective group at the 7-position is triethylsilyl ether, hydrolysis with hydrochloric acid in methanol or hydrofluoric acid and pyridine in acetonitrile can successfully be used.

13-Keto-baccatin III can conveniently be prepared by oxidation of baccatin III. Oxidation of baccatin III can be carried out with ozone, or with manganese dioxide in aprotic solvents such as methylene chloride, tetrahydrofuran, acetone, ethyl acetate. The reaction can be carried out at 0° C.–60° C., more preferably at room temperature.

The processes of the invention are summarized in the following scheme:

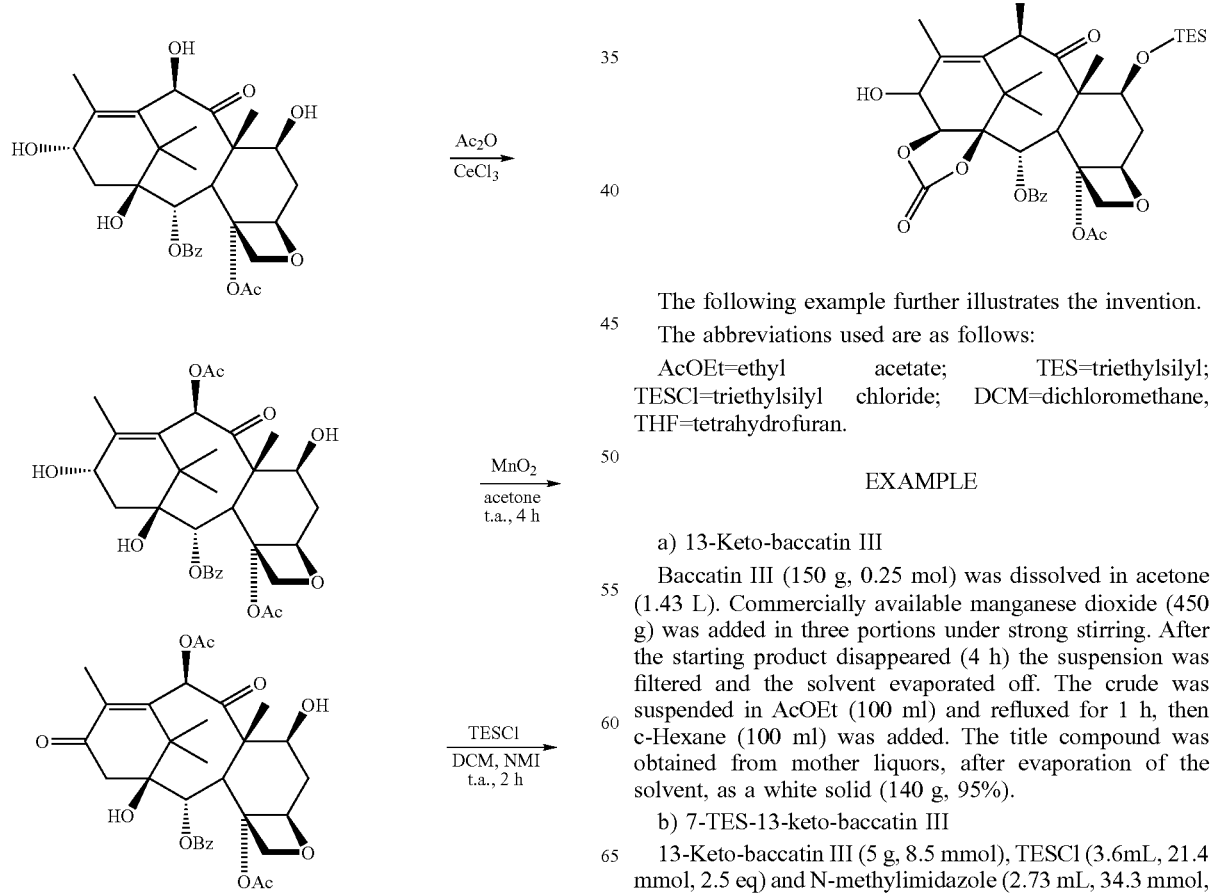

The following example further illustrates the invention.

The abbreviations used are as follows:

AcOEt=ethyl acetate; TES=triethylsilyl; TESCl=triethylsilyl chloride; DCM=dichloromethane, THF=tetrahydrofuran.

EXAMPLE a) 13-Keto-baccatin III

Baccatin III (150 g, 0.25 mol) was dissolved in acetone (1.43 L). Commercially available manganese dioxide (450 g) was added in three portions under strong stirring. After the starting product disappeared (4 h) the suspension was filtered and the solvent evaporated off. The crude was suspended in AcOEt (100 ml) and refluxed for 1 h, then c-Hexane (100 ml) was added. The title compound was obtained from mother liquors, after evaporation of the solvent, as a white solid (140 g, 95%).

b) 7-TES-13-keto-baccatin III

13-Keto-baccatin III (5 g, 8.5 mmol), TESCl (3.6mL, 21.4 mmol, 2.5 eq) and N-methylimidazole (2.73 mL, 34.3 mmol, 4 eq) were dissolved in anhydrous DCM (25 ml). The solution was left under stirring for 1.5 h then quenched by slowly pouring it into 2M NaHSO$_4$ (25 ml). The aqueous layer was washed, extracted with DCM (2×10 ml) and the combined organic layers were extracted with brine (2×20 ml). The organic solution was dried over sodium sulfate to give 4.7 g of the title compound, sufficiently pure for the subsequent step. M.p.: 212° C. TLC: cHex-AcOEt 1:1, Rf=0.57. $^1$H-NMR (200 MHz, CDCl$_3$) δ 0.58–0.66 (m, 6H, Si—CH$_2$); 0.90–0.98 (t, J=8.4, 9H, CH$_2$CH$_3$); 1.21 (s, 3H, 17-Me); 1.27 (s, 3H, 16,-Me); 1.69 (s, 3H, 19-Me); 1.83–1.96 (m, 1H, 6-H); 2.20 (s, 3H, 18-Me); 2.21 (s, 3H, 10-OAc); 2.25 (s, 3H, 4-OAc); 2.48–2.65 (m, 1H, 6-H); 2.81 (ABq, 2H, 14-H); 3.93 (d, J=6.6, 1H, 3-H); 4.25 (ABq, 2H, 20-H); 4.51 (dd, J=10.6, 7.0, 1H, 7-H); 4.94 (d, J=7.7, 1H, 5-H); 5.72 (d, J=7.0, 1H, 2-H); 6.61 (s, 1H, 10-H); 7.52 (t, J=6.2, 2H, Bz); 7.64 (t, J=6.2, 11H, Bz); 8.10 (dd, J=7.4, 1.1, 2H, Bz).

c) 14-Hydroxy-7-TES-13-keto-baccatin III

7-TES-13-keto-baccatin III (670 mg, 0.96 mmol) was dissolved in a mixture of anhydrous THF (9 ml) and DMPU (2 ml) and cooled to −60° C. under N$_2$. A 1M solution of t-BuOK in THF (2.5 ml, 0.86 mmol), previously cooled to −50° C., was dropped therein. This solution was stirred at −60° C. for 45 minutes, then added drop by drop with (±)-camphorsulfonyl-oxaziridine (440 mg, 2 mmol) dissolved in anhydrous THF (2 ml). The reaction mixture was stirred for 3 hours at −60° C. then quenched with a 10% AcOH solution in anhydrous THF (2 ml). The mixture was then left to warm at room temperature, then extracted with DCM (2×10 ml). The combined organic layers were washed with water, a NaCl saturated aqueous solution of (15 ml) and dried over Na$_2$SO$_4$. The title compound was purified by flash chromatography (silica gel, cHex-AcOEt, 8:2) in a 79% yield. Alternatively, this was used directly in the subsequent step without further purification. M.p.: 94–98° C. TLC: cHex-AcOEt 1:1, Rf=0.5. $^1$H-NMR (200 MHz, CDCl$_3$) δ 0.58–0.66 (m, 6H, Si—CH$_2$); 0.91–0.99 (t, J=8.7, 9H, CH$_2$CH$_3$); 1.24 (s, 3H, 17-Me); 1.28 (s, 3H, 16,-Me); 1.75 (s, 3H, 19-Me); 1.83–2.05 (m, 1H, 6-H); 2.14 (s, 3H, 18-Me); 2.24 (s, 3H, 10-OAc); 2.26 (s, 3H, 4-OAc); 2.46–2.61 (m, 1H, 6-H); 3.64 (s, 1H, 1-OH) 3.73 (d, J=1.8, 1H, 14-OH); 3.87 (d, J=6.9, 1H, 3-H); 4.14 (d, J=1.8, 1H, 14-H); 4.31 (s, 2H, 20-H); 4.49 (dd, J=10.7, 6.6, 1H, 7-H); 4.93 (d, J=7.3, 1H, 5-H); 5.89 (d, J=7.0, 1H, 2-H); 6.53 (s, 1H, 10-H); 7.46–7.66 (m, 3H, Bz); 8.08 (dd, J=7.0, 1.5, 2H, Bz)

d) 14β-Hydroxy-7-TES-13-keto-baccatin III 1,14-carbonate

A solution of 14β-hydroxy-7-TES-13-keto-baccatin (12.2 g) in anhydrous DCM (50 ml) and pyridine (16 ml) was dropped in a 20% phosgene solution in DCM (45 mL, 5 eq) at −10° C. After 2 hours the reaction was added drop by drop with a 5% NaHCO$_3$ aqueous solution (100 ml). The aqueous layer was washed with DCM (3×50 ml) and the crude was purified by flash chromatography (silica gel, DCM-AcOEt=50:1) to give the title compound in a 95% yield. M.p.: 97–99° C. TLC: cHex-AcOEt 1:1, Rf=0.64. $^1$H-NMR (200 MHz, CDCl$_3$) δ 0.58–0.66 (m, 6H, Si—CH$_2$); 0.91–0.99 (t, J=8.7, 9H, CH$_2$CH$_3$); 1.21 (s, 3H, 17-Me); 1.39 (s, 3H, 16,-Me); 1.75 (s, 3H, 19-Me); 1.86–2.13 (m, 1H, 6-H); 2.22 (s, 3H, 18-Me); 2.25 (s, 3H, 10-OAc); 2.26 (s, 3H, 4-OAc); 2.48–2.63 (m, 1H, 6-H); 3.83 (d, J=7.0, 1H, 3-H); 4.30 (ABq, 2H, 20-H); 4.49 (dd, J=11.0, 7.0, 1H, 7-H); 4.81 (s, 1H, 14-H); 4.93 (d, J=7.3, 1H, 5-H); 6.15 (d, J=7.0, 1H, 2-H); 6.54 (s, 1H, 10-H); 7.51 (t, 2H, Bz); 7.62–7.70 (m, 1H, Bz); 8.01 (dd, J=7.0, 1.9, 2H, Bz).

e) 14β-Hydroxy-7-TES-baccatin III 1,14-carbonate

A suspension of NaBH$_4$ (0.5 g) in absolute ethanol (10 ml) was cooled to −50° C., and added with a cooled solution of 14-hydroxy-7-TES-13-keto-baccatin III 1,14-β-carbonate (0.5 g, 0.6 mmol) in absolute ethanol (10 ml). After the starting product disappeared (8 h), the reaction was quenched with citric acid and extracted with AcOEt. The combined organic layers were dried over sodium sulfate and the solvent was evaporated off. The title compound was obtained as a white solid in an 85% yield, after chromatography. M.p.: 134–137° C. TLC: cHex-AcOEt 1:1, Rf=0.46. $^1$H-NMR (200 MHz, CDCl$_3$) δ 0.58–0.66 (m, 6H, Si—CH$_2$); 0.91–0.99 (t, J=8.7, 9H, CH$_2$CH$_3$); 1.16 (s, 3H, 17-Me); 1.28 (s, 3H, 16,-Me); 1.74 (s, 3H, 19-Me); 1.85–2.14 (m, 1H, 6-H); 2.06 (s, 3H, 18-Me); 2.21 (s, 3H, 10-OAc); 2.33 (s, 3H, 4-OAc); 2.47–2.65 (m, 1H, 6-H); 3.74 (d, J=7.4, 1H, 3-H); 4.12–4.35 (m, 2H, 20-H); 4.49 (dd, J=10.3, 6.6, 1H, 7-H); 4.82 (d, 1H, 14-H); 4.99 (d, J=7.3, 1H, 5-H); 5.00–5.03 (m, 1H, 13-H); 6.11 (d, J=7.4, 1H, 2-H); 6.45 (s, 1H, 10-H); 7.50 (t, 2H, Bz); 7.60–7.68 (m, 1H, Bz); 8.04 (dd, J=7.0, 1.5, 2H, Bz).

f) 14β-Hydroxy-baccatin III 1,14-carbonate

14-Hydroxy-7-TES-baccatin III 1,14-β-carbonate (9.6 g, 1.3 mmol) was dissolved in a mixture of acetonitrile (5.4 ml) and pyridine (6.4 ml) cooled to 0° C. A solution of 70% HF in pyridine (0.95 ml) was dropped in 15 min and the solution was stirred at room temperature overnight. The reaction mixture was then poured into 20 mL of ice and left under stirring for 1 h, then extracted with DCM (3×10 ml) and the combined organic layers were washed with 10% NaHSO$_4$ (to pH=2), 5% NaHCO$_3$ (2×10 ml) and brine (2×10 ml). After evaporation of the solvent, the title compound was obtained as a white solid in a 96% yield.

What is claimed is:

1. A process for the preparation of 14β-hydroxy-1,14-carbonate-baccatin III, which comprises:

a. treatment of 7-triethylsilyl-13-ketobaccatin III of formula

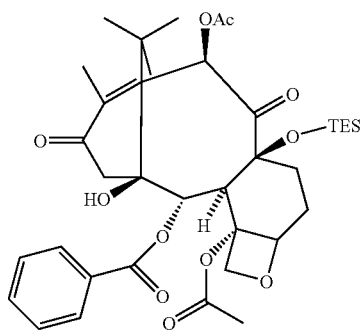

with suitable bases and oxidizing agents, to give 7-triethylsilyl-13-keto-14-hydroxy-baccatin III:

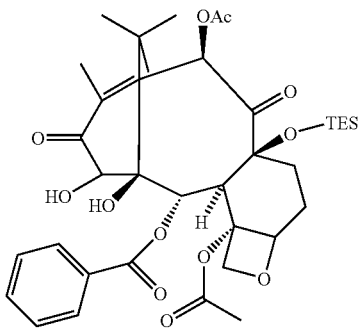

b. carbonation of the 1 and 14 hydroxyls to give 14β-Hydroxy-7-TES-13-keto-baccatin III-1,14-carbonate:

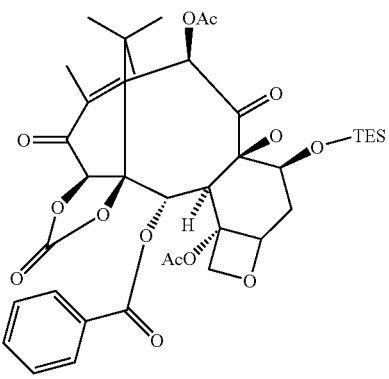

c. reduction of the ketone at the 13-position and cleavage of the protective group in 7.

2. The process as claimed in claim 1 wherein step a) is carried out by treatment with potassium t-butoxide or potassium bis(trimethylsilyl)amide at a temperature from −40 to −78° C. in ethers in admixture with hexamethylphosphoramide (HMPA) or 1,3-dimethyl-3,4,5,6-tetrahydro-2(1H)pyrimidinone (DMPU), in the presence of oxaziridine derivatives.

3. The process as claimed in claim 2 wherein the oxaziridine derivative is selected from N-benzenesulfonyl phenyl oxaziridine, N-benzenesulfonyl m-nitrophenyl oxaziridine and camphorsulfonyloxaziridine.

4. The process according to claim 1, wherein step b) is carried out by treatment with a carbonyldiimidazole or phosgene in chlorinated solvents in the presence of a base at temperatures ranging from −40° C. to room temperature.

5. The process according to claim 1, wherein step c) is carried out by treatment with a hydride at a temperature from −20 to −50° C.

6. The process as claimed in claim 5 wherein the hydride is selected from sodium borohydride, lithium borohydride, sodium triacetoxy borohydride and the reaction is carried out in ethanol, methanol, isopropanol, or in a methanol and tetrahydrofuran mixture.

7. The process according to claim 1, wherein 13-keto-baccatin III protected at the hydroxyl in 7 is prepared by selective acetylation of the hydroxyl 10 followed by oxidation of the hydroxyl 13 and protection of the hydroxyl 7.

8. The process as claimed in claim 7 wherein 13-keto-baccatin III is obtained by selective acetylation of deacetyl-baccatin III with acetic anhydride followed by oxidation with manganese dioxide in aprotic solvents at 0° C.–60° C.

9. A compound of formula:

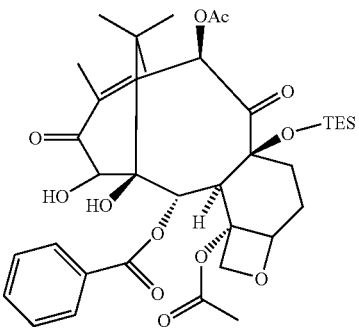

10. A compound 14β-Hydroxy-7-TES-13-keto-baccatin III-1,14-carbonate, of formula:

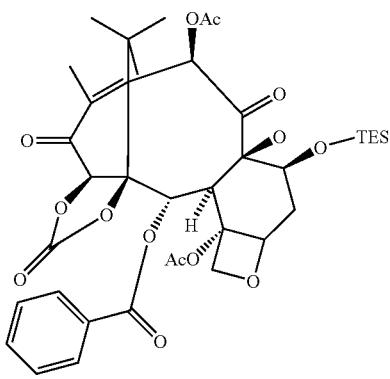

11. The process according to claim 2, wherein step b) is carried out by treatment with a carbonyldiimidazole or phosgene in chlorinated solvents in the presence of a base at temperatures ranging from −40° C. to room temperature.

12. The process according to claim 3, wherein step b) is carried out by treatment with a carbonyldiimidazole or phosgene in chlorinated solvents in the presence of a base at temperatures ranging from −40° C. to room temperature.

13. The process according to claim 2, wherein step c) is carried out by treatment with a hydride at a temperature from −20 to −50° C.

14. The process according to claim 3, wherein step c) is carried out by treatment with a hydride at a temperature from −20 to −50° C.

15. The process according to claim 4, wherein step c) is carried out by treatment with a hydride at a temperature from −20 to −50° C.

16. The process according to claim 2, wherein 13-keto-baccatin III protected at the hydroxyl in 7 is prepared by selective acetylation of the hydroxyl 10 followed by oxidation of the hydroxyl 13 and protection of the hydroxyl 7.

17. The process according to claim 3, wherein 13-keto-baccatin III protected at the hydroxyl in 7 is prepared by selective acetylation of the hydroxyl 10 followed by oxidation of the hydroxyl 13 and protection of the hydroxyl 7.

18. The process according to claim 4, wherein 13-keto-baccatin III protected at the hydroxyl in 7 is prepared by selective acetylation of the hydroxyl 10 followed by oxidation of the hydroxyl 13 and protection of the hydroxyl 7.

19. The process according to claim 5, wherein 13-keto-baccatin III protected at the hydroxyl in 7 is prepared by selective acetylation of the hydroxyl 10 followed by oxidation of the hydroxyl 13 and protection of the hydroxyl 7.

20. The process according to claim 6, wherein 13-keto-baccatin III protected at the hydroxyl in 7 is prepared by selective acetylation of the hydroxyl 10 followed by oxidation of the hydroxyl 13 and protection of the hydroxyl 7.

* * * * *